United States Patent [19]

Kashman et al.

[11] Patent Number: 5,661,175
[45] Date of Patent: Aug. 26, 1997

[54] HEMIASTERLIN AND GEODIAMOLIDE TA

[76] Inventors: Yoel Kashman, Tel-Aviv University, Tel-Aviv, Israel; Dolores G. Gravalos, de la Calera No. 3, Tres Cantos, Madrid, Spain

[21] Appl. No.: 492,726

[22] Filed: Jun. 20, 1995

[51] Int. Cl.$^6$ .......................... A61K 31/40; C07D 209/14
[52] U.S. Cl. ................ 514/419; 514/183; 540/1; 548/495
[58] Field of Search .................... 548/496, 495; 514/419, 183; 540/1

[56] References Cited

PUBLICATIONS

Crews et al., *Tetrahedron Letters* vol. 27, No. 25, pp. 2797–2800, 1986.
Chan et al., *J. Org. Chem.*, 52:3091–3093, 1987.
Grieco et al., *Tetrahedron Letters*, vol. 29, No. 34, pp. 4225–4228, 1988.
de Silva et al., *Tetrahedron Letters*, vol. 31, No. 4, pp. 489–492, 1990.
Stingl et al., *Cancer Chemother Pharmacol*, 30:401–406, 1992.
Rao et al., *Tetrahedron Letters*, vol. 34, No. 44, pp. 7081–7084, 1993.
Rao et al., *Tetrahedron Letters*, vol. 34, No. 44, pp. 7085–7088, 1993.
Imaeda et al., *Tetrahedron Letters*, vol. 35, No. 4, pp. 591–594, 1994.
Talpir et al., *Tetrahedron Letters*, vol. 35, No. 25, pp. 4453–4456, 1994.

*Primary Examiner*—Jacqueline Haley
*Attorney, Agent, or Firm*—Ernest V. Linek

[57] ABSTRACT

Three cytotoxic peptides, the known compound Jaspamide and two new peptides, hemiasterlin (Compound 2) and geodiamolide TA (Compound 3), have been isolated from the sponge *Hemiasterella minor*. The structures of the three were determined by interpreting the NMR and mass spectra. Hemiasterlin (Compound 2) is a novel linear tripeptide embodying two unique, new natural amino acids and geodiamolide TA (Compound 3) is a newly discovered higher homolog of geodiamolides A–F.

14 Claims, No Drawings

HEMIASTERLIN AND GEODIAMOLIDE TA

BACKGROUND OF THE INVENTION

The present invention is directed to the isolation and identification of two new compounds, Hemiasterlin and Geodiamolide TA, two new cytotoxic peptides isolated from the marine sponge *Hemiasterella minor* (Kirkpatrick), as well as pharmaceutical compositions comprising these compounds and a suitable carrier or diluent.

SUMMARY OF THE INVENTION

The sponge *Hemiasterella minor* (Kirkpatrick) (class, Demospongiae; order, Hadromerida; family, Hemiasterllidae) collected in Sodwana Bay, north to Durban, South Africa, contains a variety of bioactive compounds.

The major metabolite in four examined specimens was found, on the basis of its spectral data, to be the earlier reported bioactive cyclic depsipeptide jaspamide (asplkinolide) (Compound 1) isolated from *Jaspis sp.* (order, Astrophoride (Choristida))[1] (0.2%, dry wt.). Two of the sponge samples studied contained minute amounts of a second peptide, hemiasterlin (Compound 2) and one specimen a third compound, geodiamolide TA (Compound 3). These two newly isolated compounds (Compounds 2 and 3), and pharmaceutical compositions containing the same, form the basis of this invention.

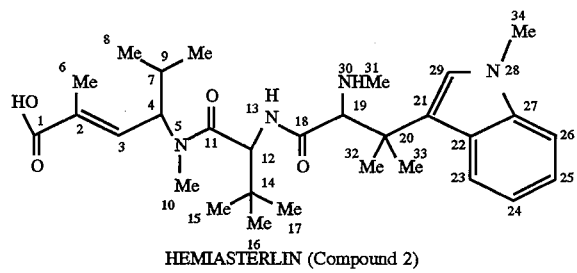

HEMIASTERLIN (Compound 2)

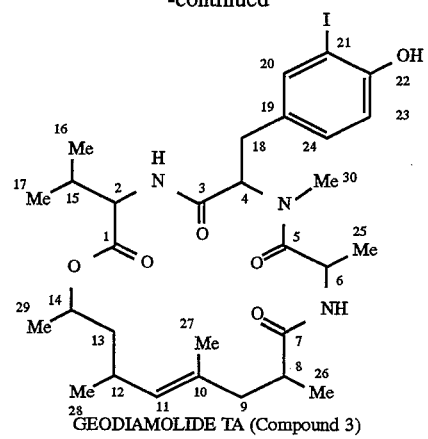

GEODIAMOLIDE TA (Compound 3)

DETAILED DESCRIPTION OF THE PREFERRED EMBODIMENTS

Freshly collected Hemiasterella minor was frozen on site and kept frozen until needed. Freeze-dried sponge tissue (60 g, dry wt.) was extracted sequentially with hexane, ethyl acetate and ethyl acetate/MeOH, 1:1. The latter two extracts were subsequentially partitioned between aqueous methanol (1:1, MeOH/H$_2$O) and chloroform and the chiroform soluble portion was fractionated by sequential application of Sephadex LH-20 (2L1L1:hexane/MEOH/CHCl$_3$ and reversed phase HPLC (MeOH/H$_2$O,90:10) chromatographies to give samples of jaspamide (1)[1], hemiasterlin (2) and geodiamolide TA (3) (120 mg, 6 mg and 2 mg, respectively), from one of the specimens which contained all three).

Structure elucidation of Compound 2[2] was begun by intensive study of spectrometric data. The molecular formula C$_{30}$H$_{47}$N$_4$O$_4$ (MH$^+$) was established by HRFABMS ("magic bullet") and by the C and H count obtained from NMR. The $^{13}$C NMR (CDCl$_3$) revealed its functional groups, as follows: (a) an indole heterocycle ($\delta$121.0 s, 127.5 d, 139.2 s, 109.5 d, 122.3 d, 119.1 d, 121.2 d and 127.0 s); (b) three carbonyls ($\delta$ 172.1, 172.5, 173.1); (c) a double bond ($\delta$131.1 s, 140.1 d); and (d) eleven methyls including three N-Me's, one vindyl-methyl, a gem-dimethyl group, one iso-propyl and one tert-butyl group (see Table 1).

According to the ten degrees of unsaturation of Compound 2 and the above functionalities, hemiasterlin has to be linear. 2D NMR spectra, i.e., COSY, HMQC, HMBC and TOSCY experiments (see Table 1) revealed the three substructures A–C containing the above functional groups).

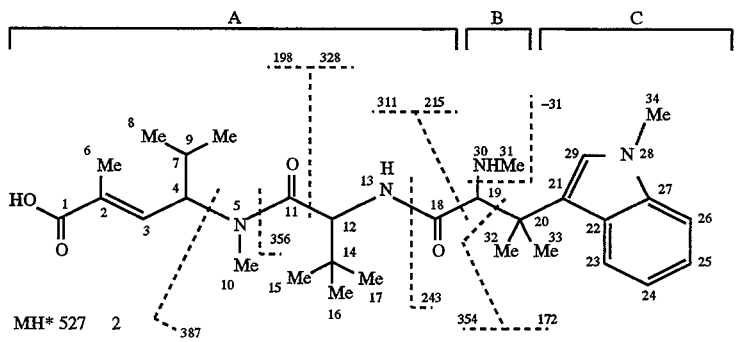

Furthermore, CH-correlations from and to the CH(19) NHCH$_3$ moiety (B) ($\delta_c$ 73.2, $\delta_H$, 3.60) suggested the latter group to be the linkage between substructures A and C.

Unequivocal proof for the linear tripeptide structure of Compound 2 was achieved from the MS/MS data. Mass measurement of the parent ion gave MH$^+$527.3579 (calc. 527.3579 C$_{30}$H$_{47}$N$_4$O$_4$). The regular FAB mass spectrum and the B/E linked scan spectrum of the protonated parent ion were similar and the major ions were assignable to the structure. Loss of methylamine (see "-31") dominated much of the fragmentation observed, and is first observed from the parent ion at 496. The base peak at 172 arises from the methylated tryptamine moiety and is, as expected, quite stable so no significant further fragmentation is observed below this. The complementary species was also observed at 354, but smaller as expected. Further pairs of ions were observed where the break was to the carbonyl and β to the nitrogen. These are at 215/311 and 328 (observed as 927-31)/198. The remaining significant fragments at 356 and 387 add further proof to the structure. In all cases the ions containing the methylamine fragment lost this as a neutral fragment (387→356 [indistinguishable from the 356 fragment], 356→325 and 215→184 [this was far more predominant in the normal FAB spectrum]). The ion at 354 does not loose 31 which is expected due to the methylamine nitrogen being involved in the stabilizing of the ion.[3]

Besides t-Leu earlier discovered in the discodermins[4] and before only reported as a constituent of the actinomycete peptides bottomycins[5], hemisterlin (Compound 2) contains two other unique amino acids i.e., the γ-amino acid 4-amino-2,5dimethylhex-2-enoic acid and N,N',β,β-tetramethyltryptophan.

Of special interests in the IR spectrum of Compound 2, was the absence of a broad 330–2600 cm$^{-1}$ absorption of the CO$_2$H group, suggesting a carboxylate ion[6]. The presence of the carboxylic group, though, was confirmed by micro-scale methylation of Compound 2 with CH$_2$N$_2$ to afford the corresponding methyl ester ($\delta_c$ 52.1, $\delta_H$ 3.75). The above observations together with the low-field NMR signals of the C19-methine group suggested a zwitterion between the spatially close carboxylic and amino groups. Indeed, acetylation of the C19-amine (AC$_2$ O/Pyr., rt) brought to the discovery of the CO$_2$H absorption at 3300b cm$^{-1}$ and a 12 ppm up-field shift of the C19 resonance[7]. Final proof for the suggested cyclic conformation of the C1-C19 backbone of Compound 2 was achieved from a NOE between Me-6 and Me-31[8].

Geodiamolide TA (Compound 3)[9], isolated as a colorless glass (2 mg), [a]$_D$+30 (c 0.027.CHCl$_3$), gave a parent ion in the HRMS at m/z 670.2335 (MH$^+$) corresponding to a molecular formula of C$_{30}$H$_{44}$N$_3$O$_6$I. Fragmentation of the structure is summarized in the Figure. The parent ion (L:X=1) dehalogenated under the FAB conditions to yield I:X=H at m/z 544.3379 (24%, calc. 544.3387 (24%, calc. 544.3387 C$_{30}$N$_{46}$N$_3$O$_6$). Further fragmentation was observed from both species; they gave ions with structure II at m/z 421.00638 (17%, calc. 421.00625 C H N O I) and m/z 295.1667 (5%, calc. 295.1658 C$_{15}$N$_{23}$N$_2$O$_4$); and ions with structure III at m/z 275.9876 (31%, calc. 275.9886 C$_9$H$_{11}$NOI) and m/z 150 (12%, C$_9$H$_{12}$NO) (respectively X=1, X=H)[10].

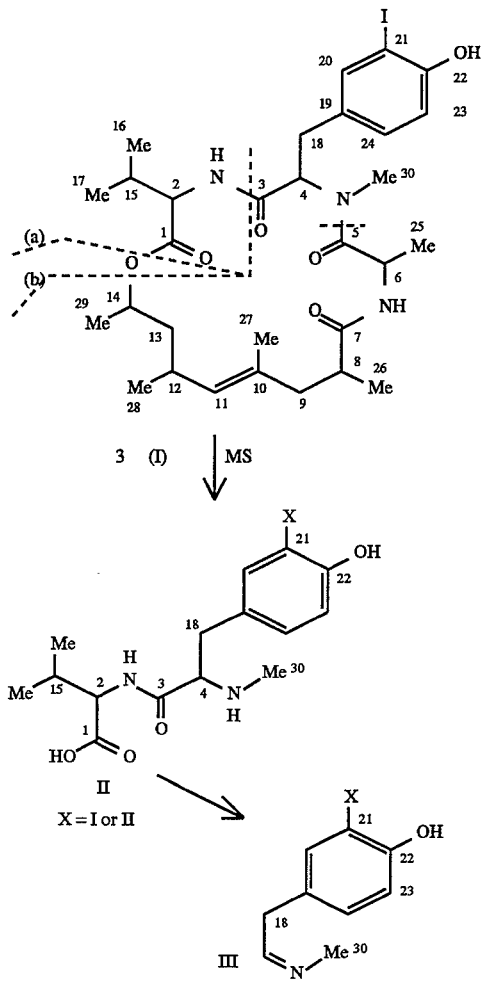

Resonances in the $^1$H and $^{13}$C NMR spectra of Compound 3 (Table 2) could be assigned to a 12-carbon polypropinate unit (C7 to C14 with the attached methyls) identical to the one found in geodiamolides characteristic-value of 86 ppm for the iodine bearing C-atom), one alanine and one valine residue by comparison of their chemical shifts and coupling constants to those observed for geodiamolides A to F[11] and motuporin[12] (for the Val residue). 2D NMR spectra, i.e., COSY, HMQC, HMBC and TOCSY established unequivocally the complete structure of Compound 3, that is, the Ala residue in geodiamolide D[9] being replaced by a Val residue in geodiamolide TA. The similarity in the NMR data of Compound 3 and the geodiamolides implied that the chiral centers in geodiamolide TA and the same relative configurations as in geodiamolides A to F[11].

TABLE 1

NMR Data of Hemiasterlin (Compound 2) in CDCl$_3$ (500 Mhz)

| No. | $^{13}$C, ppm | $^1$H,ppm | HMBC | |
|---|---|---|---|---|
| | COSY | (multi;J(Hz)) | (to C#) | (to H#) |
| 1 | 172.1 s | | | |
| 2 | 131.1 s | | | |
| 3 | 140.1 d | 6.73 (d,9.8) | 6.1 | 4 |
| 4 | 56.3 d | 5.11 (t,9.8) | 11,10,9 8,7,3,2 | 7.3 |

TABLE 1-continued

NMR Data of Hemiasterlin (Compound 2) in CDCl₃ (500 Mhz)

| No. | $^{13}C$, ppm | $^1H$,ppm | HMBC | |
|-----|---------|---------|---------|---------|
| COSY | | (multi;J(Hz)) | (to C#) | (to H#) |
| 6 | 14.6 q | 1.90 (s) | 3,2,1 | |
| 7 | 30.3 q | 1.86 (m) | 9,8,4 | |
| 8 | 19.5 q | 0.79 (d,6.0) | 9,7,4 | 7 |
| 9 | 19.0 q | 0.86 (d,6.0) | 8,7,4 | 7 |
| 10 | 31.4 q | 3.06 (s) | 11,4 | |
| 11 | 175.2 d | | | |
| 12 | 55.2 d | 4.88 (d,9.8) | 17,16,15 14,11 | NH(13) |
| 14 | 35.5 s | | | |
| 15 | 27.2 q | 1.00 (s) | 17,16,14,12 | |
| 16 | 27.2 q | 1.00 (s) | 17,15,14,12 | |
| 17 | 27.2 q | 1.00 (s) | 16,15,14,12 | |
| 18 | 173.1 s | | | |
| 19 | 73.2 d | 3.60 (s) | 33,32,31,21,20,18 | |
| 20 | 38.4 s | | | |
| 21 | 127.0 s | | | |
| 22 | 127.0 s | | | |
| 23 | 121.2 d | 7.90 (d,8.3) | 27,25,22 | 24 |
| 24 | 119.1 d | 7.08 (t,7.5) | 26,22 | 25,24 |
| 25 | 123.3 d | 7.22 (t,7.5) | 27,23 | 26,24 |
| 26 | 109.5 d | 7.29 (d,8.3) | 24,22 | 25 |
| 29 | 127.5 d | 6.86 (s) | 34,27,26,22, 20,19 | |
| 31 | 36.0 q | 2.00 (s) | 19 | |
| 32 | 23.5 q | 1.44 (s) | 33,29,21, 20,19 | 33 |
| 33 | 28.2 q | 1.60 (s) | 32,21,20,19, | 32 |
| 34 | 33.1 q | 3.75 (s) | 29,27 | |
| NH(13) | | 7.90 (d,8.3) | 18,15 | 12 |

TABLE 2

NMR Data of geodiamolide TA (Compound 3) in CDCl₃ 1500 MHz)

| No. | $^{13}C$.ppm | $^1H$.ppm | HMBC | |
|-----|---------|---------|---------|---------|
| COSY | | (multi;J(Hz)) | (to C#) | (to H#) |
| 1 | 170.0 s | | | |
| 2 | 58.6 d | 4.25 (dd,6.9) | 1,15 | 14,NH(2) |
| 3 | 169.5 s | | | |
| 4 | 57.2 d | 5.18 (t,7) | 3.5.19 | 18,18',20 |
| 5 | 174.7 s | | | |
| 6 | 46.8 d | 4.67 (quin,6.5) | 7,25 | 25,NH(6) |
| 7 | 175.2 s | | | |
| 8 | 42.1 d | 2.23 (m) | 9,9',26 | |
| 9 | 42.5 t | 1.98 (m) | 7,8,10,11,26 | 8,9' |
| 9' | | 2.06 (m) | 7,8,10,11,26 | 8,9' |
| 10 | 133.5 s | | | |
| 11 | 132.0 d | 4.86 (d,8.5) | 9,27 | 12 |
| 12 | 29.0 d | 2.06 (m) | 10,11 | 11,13,13' |
| 13 | 43.6 t | 1.30 (m) | 12,14,28,29 | 12,13',14 |
| 13' | | 1.60 (m) | 12,13,14 | |
| 14 | 71.7 d | 4.78 (sext,7) | 13,13',29 | |
| 15 | 32.0 d | 1.98 (m) | | 2,16,17 |
| 16 | 17.8 q | 17.8 q 0.75(d,6.5) | 2,15,17 | |
| 15,17 | | | | |
| 17 | 18.7 q | 0.77 (d,6.5) | 2,15,16 | 15,17 |
| 18 | 32.2 t | 32.2 t 2.82(dd,14.5,8) | 3,4,20,24 | 4,18' |
| 18' | | 3.08 (dd,14.5,8) | 3,4,20,24 | 4,18' |
| 19 | 130.5 s | | | |
| 20 | 138.8 d | 7.42 (d,2) | 18,22,24 | 4,24 |
| 21 | 86.2 s | | | |
| 22 | 154.5 s | | | |
| 23 | 115.1 d | 6.82 (d,8) | 19,20,22 | 24 |
| 24 | 131.1 d | 7.01 (d,8) | 18,20,22 | 20,23 |
| 25 | 18.8 q | 1.04 (d,6.5) | 5,6 | 6 |
| 26 | 18.5 q | 1.09 (d,6.5) | 7,8,9 | 8 |
| 27 | 17.7 q | 1.46 (s) | 9,11 | |
| 28 | 20.5 q | 0.79 (d,6.5) | 11,13 | 12 |

TABLE 2-continued

NMR Data of geodiamolide TA (Compound 3) in CDCl₃ 1500 MHz)

| No. | $^{13}C$.ppm | $^1H$.ppm | HMBC | |
|-----|---------|---------|---------|---------|
| COSY | | (multi;J(Hz)) | (to C#) | (to H#) |
| 29 | 20.6 q | 1.16 (d,6.5) | 13,14 | 14 |
| 30 | 30.5 q | 2.97 (s) | 4,5 | |
| NH(2) | | 6.32 (d,6.5) | 3 | 6 |
| NH(6) | | 6.44 (d,6.5) | 7 | 2 |

All three peptides isolated from the sponge (Compounds 1–3) showed cytotoxicities against several cell lines; e.g., in concentration of ca. 0.01 μu/ml against P388 cells, however, as Compounds 2 and 3 might have contained impurities of Compound 1, the assays were repeated when additional amounts of Compounds 2 and 3 became available.

Isolation of Compounds 1 and 3 from taxonomically remote species (orders Choristida, Axinellida and now Hadromerida) together with the presence of the t-Leu residue in Compound 2, vide supra, suggests, as already mentioned earlier[12] an involvement of symbionts in the production of peptide compounds 1 and 3.

Cell Cultures

Cells were maintained in logarithmic phase of growth in Eagle's Minimum Essential Medium, with Earle's Balanced Salts, with 2.0 mM L-Glutamine, with non-essential Amino Acids, without Sodium Bicarbonate (EMEM/NEAA); supplemented with 10% Fetal Calf Serum (FCS), 10–2M Sodium Bicarbonate and 0.1 g/l Penicillin-G+Streptomycin Sulfate.

A simple screening procedure has been carried out to determine and compare the antitumor activity of these compounds, using an adapted form of the method described by Bergeron et al. (1984). The antitumor cell employed have been P-388 (suspension culture of a lymphoid neoplasm from DBA/2 mouse), A-549 (monolayer culture of a human lung carcinoma), HT-29 (monolayer culture of a human colon carcinoma) and MEL-28 (monolayer culture of a human melanoma).

P-388 cells were seeded into 16 mm wells at $1\times10^4$ cells per well in 1 ml aliquots of MEM 5FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, an approximately $IC_{50}$ was determined by comparing the growth in wells with drug to the growth in wells control.

A-549, HT-29 and MEL-28 were seeded into 16 mm wells at $2\times10^4$ cells per well in 1 ml aliquots of MEM 10FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, the wells were stained with 0.1% Crystal Violet. An approximately $IC_{50}$ was determined by comparing the growth in wells with drug to the growth in wells control.

The following table (Table 3) shows the biological activity of Compound 3 (Geodiamolide TA) against several tumor cell lines:

TABLE 3

| | IC$_{50}$ µg/ml | | | |
|---|---|---|---|---|
| Cell Lines | P388 | A549 | HT29 | MEL28 |
| GEODIAMOLIDE | 0.01 | 0.01 | 0.005 | 0.01 |

See, Bergeron et al., Antineoplastic and antiherpetic activity of spermidine catecholamide iron chelators, Biochem. Bioph. Res. Comm. 121 (3), 848–854 (1984) and Schroeder et al., Effects of Acyclic Pyrimidine Nucleoside Analoges, J. Med. Chem., 24, 1078–1083 (1981).

Therefore, the present invention also provides a method of treating any mammal affected by a malignant tumor sensitive to the compounds of the present invention, which comprises administering to the affected individual a therapeutically effective amount of these compounds or a pharmaceutical composition comprising one or both of said compounds and an acceptable diluent or carrier therefor. Thus the present invention also comprises pharmaceutical preparations which contain as an active ingredient, one or more of the compounds of this invention, or pharmaceutically acceptable salts thereof.

Examples of pharmaceutical compositions include any solids (tablets, pills, granules, etc.) or liquids (solutions, suspensions, or emulsions), suitable compositions for oral, topical or parenteral administration, and they may contain the pure compound or the compound in combination with a carrier or other pharmacologically active compounds.

The correct dosage of a pharmaceutical composition containing the active compounds of the present invention will vary according to the particular formulation, the mode and situs of administration, host and tumor being treated. Other factors which the skilled artisan will recognize as important include the age, body weight, sex, diet, time of administration, rate of excretion, condition of the host, other drug combinations, reaction sensitivities, and the like. Administration of the active compounds of the present invention can be carried out continuously or periodically within the calculated maximum tolerated dose.

REFERENCES [INFORMATION DISCLOSURE]

Several publications have been referenced herein (see footnote numbers), and the disclosures thereof are hereby incorporated herein by reference. In addition the following footnotes also contain information regarding the compounds of the present invention:

1a. Zabriskie et al., J. Am. Chem. Soc., 108, 3123 (1986).

1b. Crews et al., Tetrahedron Lett., 27, 2797 (1986).

2. Glassy oil, $[\alpha]_D=95°$ (c 0.06, MeOH), IR (neat) 2965–2929, 1664, 1655, 1648, 1630, 11619 cm$^{-1}$.

3. Linked scan analysis of the fragment ion at 325 (methylamine lost) yielded 297 from loss of CO and the ions at 172 and 184 (184=215–31) while 297 itself gave 184 and a pair of complementary ions at 212 (243-31) and 86 (fragmentation of the amide bond). The ion at 215 reluctantly fragmented to 184 due to the involvement of the nitrogen lone pairs in the 215 ion. Confirmation of the above assignments and hence the structure cam from measurements of their accurate masses: meas. 387.2769 (calc. 387.2760 $C_{22}H_{35}N_4O_2$), meas. 325.1924 (calc. 325.1916 $C_{20}H_{25}N_2O_2$) meas. 297.1978 (calc. 297.1967 $C_{19}H_{25}N_2O$), meas. 215.1540 (calc. 215.1548 $C_{14}H_{19}N_2$) and meas. 172.1118 (calc. 172.1126 $C_{12}H_{14}N_2$).

4. Matsunaga et al., J. Nat. Prod., 48, 236 (1985) and Tetrahedron Lett., 25, 5165 (1984).

5. D. Schipper, J. Antiblot., 36, 1076 (1983) and references cited therein.

6. Nakanishi et al., IR Absorption Spectroscopy, Holden-Day, San Francisco, p. 38. (1977).

7. Glassy oil, IR(neat) 3363b, 1654, 1648, 1638 cm$^{-1}$; $^1$H NMR 2.26 (s, NAc); Me's; 1.93 (s), 0.91 (d,6), 0.90 (d,6), 2.99 (s, NMe), 0.47 (s, tBu), 1.45 (s), 1.63 (s), 3.79 (s, Nme); HRMS m/z 569.3725 (calc. 569.3703, $C_{32}H_{49}N_4O_3$), 369, 398 (354, 356+Ac), 285, 172.

8. Other observed NOE's (d$_6$-DMSO) for 2 are between H-10/12,3; t-Bu/12, 32, 33; H-19/NH(13), 23, 31.

9. Colorless oil, IR(neat) 3420, 1720, 1670, 1655, 1630 cm$^{-1}$.

10. Verification of this fragmentation was performed by B/E linked scan analyses which also verified that the m/z 421 (11, X=1) fragmented to give m/z (III, X=H). Additionally, this revealed a pair of fragmentations from the protonated parent ion and dehalogenated species (I, X=1 and X=H) at (a) (571.445 respectively) and (b) (553, 427 respectively) which further identified the valine. The FAB spectrum can be compared to that previously reported geodiamolide A$^{11a}$ which had an alanine in place of the valine (m/z 670:642, 544:51 6, 421:393, 276;276, 150:150 for geodiamolide TA compared to geodiamolide A).

11a. Chan et al., J. Org. Chem., 52, 3091 (1987).

11b. Dilpde et al., Tetrahedron Lett., 31,489 (1990).

12. Fusteani et al., Chem. Rev., 93, 1973 (1993) and references cited therein.

13. Bergeron et al., Blochem. Bioph. Res. Comm., 121 (3), 848–854 (1984).

14. Schroeder et al., J. Med. Chem, 24, 1078–1083, (1981).

The subject compounds of this invention are also disclosed in Tetrahedron Letters, Vol 35, No. 25, pages 4453–4456, published 20 Jun. 1994, the disclosure of which is hereby incorporated herein by reference.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. Hemiasterlin, substantially free of the cellular debris of its natural marine source, said compound having the following formula:

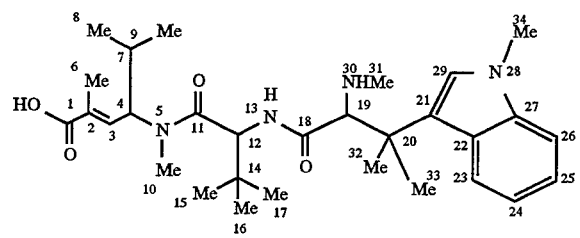

and pharmaceutically acceptable salts thereof: wherein the compound designated as hemiasterlin was extracted from the marine sponge *Hemiasterella minor* (Kirkpatrick), and purified by chromatographic means.

2. A pharmaceutical composition comprising Hemiasterlin as claimed in claim 1 and a pharmaceutically acceptable carrier or diluent.

3. A method of treating tumors in mammals comprising administering to a patient in need of such treatment, an amount of a Hemiasterlin as claimed in claim 1 or a pharmaceutically acceptable salt thereof sufficient to slow or stop the growth of the tumor cells in said patient.

4. The method of claim 3, wherein the tumor is a human lung carcinoma.

5. The method of claim 3, wherein the tumor is a human colon carcinoma.

6. The method of claim 3, wherein the tumor is a lymphcid neoplasm.

7. The method of claim 3, wherein the tumor is a human melanoma.

8. Geodiamolide TA, substantially free of the cellular debris of its natural marine source, said compound having the following formula:

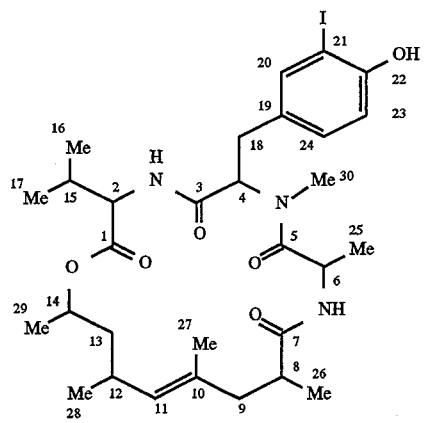

and pharmaceutically acceptable salts thereof; wherein the compound designated as geodiamolide TA was extracted from the marine sponge *Hemiasterella minor* (Kirkpatrick), and purified by chromatographic means.

9. A pharmaceutical composition comprising Geodiamolide TA as claimed in claim 8 and a pharmaceutically acceptable carrier or diluent.

10. A method of treating tumors in mammals comprising administering to a patient in need of such treatment, an amount of a Geodiamolide TA as claimed in claim 8 or a pharmaceutically acceptable salt thereof sufficient to slow or stop the growth of the tumor cells in said patient.

11. The method of claim 10, wherein the tumor is a human lung carcinoma.

12. The method of claim 10, wherein the tumor is a human colon carcinoma.

13. The method of claim 10, wherein the tumor is a lymphoid neoplasm.

14. The method of claim 10, wherein the tumor is a human melanoma.

* * * * *